(12) United States Patent
Fuchs et al.

(10) Patent No.: US 8,092,463 B2
(45) Date of Patent: Jan. 10, 2012

(54) DISTRACTION DEVICE USED FOR OSTEOGENESIS

(76) Inventors: Ernst Fuchs, Thalwil (CH); Michael Cierny, Kilchberg (CH)

( * ) Notice: Subject to any disclaimer, the term of this patent is extended or adjusted under 35 U.S.C. 154(b) by 0 days.

(21) Appl. No.: 10/508,606

(22) PCT Filed: Mar. 8, 2003

(86) PCT No.: PCT/DE03/00741
§ 371 (c)(1),
(2), (4) Date: Nov. 4, 2004

(87) PCT Pub. No.: WO03/079912
PCT Pub. Date: Oct. 2, 2003

(65) Prior Publication Data
US 2006/0058785 A1   Mar. 16, 2006

(30) Foreign Application Priority Data
Mar. 22, 2002  (DE) ................................. 102 12 815

(51) Int. Cl.
*A61B 17/60* (2006.01)
(52) U.S. Cl. .......................................... 606/90; 606/105
(58) Field of Classification Search ..................... 606/86, 606/90, 105
See application file for complete search history.

(56) References Cited

U.S. PATENT DOCUMENTS

| | | | | |
|---|---|---|---|---|
| 918,579 | A * | 4/1909 | Murch | 248/353 |
| 4,501,266 | A * | 2/1985 | McDaniel | 606/90 |
| 5,112,333 | A * | 5/1992 | Fixel | 606/62 |
| 5,213,112 | A * | 5/1993 | Niwa et al. | 600/587 |
| 5,505,733 | A * | 4/1996 | Justin et al. | 606/63 |
| 5,540,696 | A * | 7/1996 | Booth et al. | 606/88 |
| 5,597,379 | A * | 1/1997 | Haines et al. | 606/80 |
| 5,669,914 | A * | 9/1997 | Eckhoff | 606/88 |
| 5,800,438 | A * | 9/1998 | Tuke et al. | 606/90 |
| 5,902,304 | A * | 5/1999 | Walker et al. | 606/71 |
| 6,648,891 | B2 * | 11/2003 | Kim | 606/86 B |
| 6,648,896 | B2 * | 11/2003 | Overes et al. | 606/90 |
| 2004/0116930 | A1 * | 6/2004 | O'Driscoll et al. | 606/69 |
| 2006/0147492 | A1 * | 7/2006 | Hunter et al. | 424/426 |

FOREIGN PATENT DOCUMENTS

| | | | |
|---|---|---|---|
| CH | 692898 | A5 * | 12/2002 |
| EP | 1245193 | A1 * | 10/2002 |
| EP | 1457160 | A1 * | 9/2004 |
| WO | WO 0152755 | A1 * | 7/2001 |

* cited by examiner

*Primary Examiner* — Thomas C. Barrett
*Assistant Examiner* — Nicholas Woodall
(74) *Attorney, Agent, or Firm* — Edwin D. Schindler

(57) ABSTRACT

An apparatus for vertical callus distraction includes a linear drive having first and anchors, each with a plate-shaped region, that are able to be displaced relative to one another by way of the linear drive and substantially orientated perpendicularly to the direction of displacement. The first anchor is connected to a fixed bone segment and the second anchor is connected to a movable bone segment for cultivating the growth of callus between the bone segments. The linear drive has a first element with the first anchor fixed to an end of the first element, and a second element with the second anchor fixed to an end of the second element. The first and second elements are translationally displaced relative to one another with the linear drive preventing rotation of the first element relative to the second element, and preventing relative rotation between the first and second anchors.

19 Claims, 2 Drawing Sheets

DISTRACTION DEVICE USED FOR OSTEOGENESIS

BACKGROUND OF THE INVENTION

1. Field of the Invention

Figure 1A:
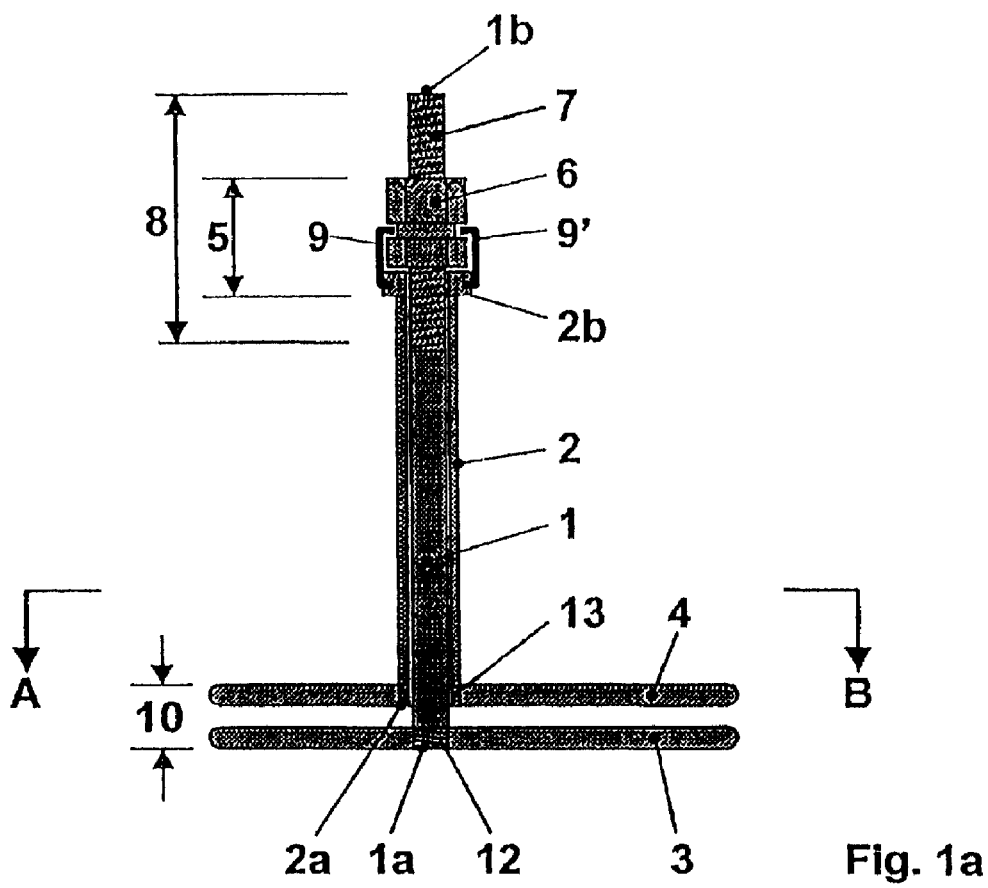

The invention relates to a device for distraction osteogenesis comprising a drive having a lead-screw and two anchors which are displaceable relative to one another by means of the drive, of which one can be connected to a fixed bone segment and one to a movable bone segment.

2. Description of the Prior Art

An area of maxillofacial surgery comprises the reconstruction of bone structures. Such measures are required in a range of illnesses, for example in severe cases of cleft lip, alveolous and palate but also Crouzon or Apert syndrome. The treatment of bone defects after trauma or tumour surgery is also dependent on the reconstruction of bones.

Conventional augmentation methods are based on the transplantation of autologous tissue. Both onlay osteoplasty and the interposition of bone or cartilage tissue are among the methods practiced according to the prior art. In this method, bone fragments are removed from regions of the body lying outside the head and inserted at the defective point in the facial or maxillary area. In the reconstruction of jaws and dentition, the aforementioned measures are usually followed by the insertion of implants.

However, the aforementioned methods have a range of disadvantages and problems, which include, inter alia, slow mineralisation and increased risk of infection of the treated body area, and a comparatively high morbidity of the removal point.

A new process for reconstruction of bone structures has become known under the name distraction osteogenesis. Instead of implantation of tissue, in this process bone tissue is obtained as new. The foundations of this method were laid by the Russian orthopaedic surgeon Ilizarov in 1988, and led to a method for extending tubular bones. This is based on pulling apart a callous formed after corticotomy at a rate of about one millimeter per day. This method activates the bone's powers of self healing, so that new callous tissue is continually produced, and thereby the tubular bone is lengthened.

Distraction osteogenesis has developed in an important therapeutic method in maxillofacial surgery. In particular, it is used for vertically building up toothless or tooth-bearing alveolar process segments and hyperatrophic lower jaws in the front-tooth and side-tooth region, or in the region of the entire lower jaw. In the execution of the aforementioned process, distraction devices are used, whose function is to continually displace a bone segment, which covers the reconstruction area and was previously operatively separated from the remaining bone, with respect to the remaining bone. The permanent displacement of the bone segment thus has the consequence that the callous forming between the sides of the displaced and fixed bone is permanently enlarged, and thereby new bone tissue is obtained. It has been found in practice that the callous is formed more intensively the smaller the distraction steps are, that is to say that it is optimum when the distraction takes place continuously. In addition to the formation of new bone, with this method the associated stretching and reproduction of the surrounding soft tissue (histogenesis) is of great advantage. It contributes substantially to the vitality of the displaced bone segment, and therefore to a reduced risk of infection and to rapid healing.

An important consideration in the development of distractors is their miniaturisation. In the distractors known in the prior art, however, this requirement disadvantageously leads to a mediocre stability of the device and less precise guidance of the anchors, which are displaceable with respect to one another.

SUMMARY OF THE INVENTION

Against this background, it is the object of the invention to provide a device for distraction osteogenesis, which avoids the aforementioned disadvantages and in particular ensures precise guidance of the anchors, which are displaceable with respect to one another, even when the device has small dimensions. Furthermore, the proposed device also permits use as tooth-implant posts that remain in the patient's jaw.

This object is achieved according to the invention in that:
the drive is designed as a linear drive,
by means of which its two elements can be translationally displaced with respect to one another without rotation,
and that one of the aforementioned anchors is fixed on the first end of one element and
the other of the aforementioned anchors is fixed on the first end of the other element.

As with distractors according to the prior art, the present distractor comprises a drive and two anchors which are displaceable relative to one another by means of the drive. Unlike the prior art, however, the drive is not embodied as a simple screw drive, but as a linear drive. This embodiment ensures that the two main elements of the drive are displaceable purely translationally with respect to one another without rotation. According to the proposal, the aforementioned anchors are in each case fixed at one end of the two elements.

For use of the device for distraction osteogenesis, one anchor is connected to the displaceable bone segment, the other to the fixed bone. The precise guidance of the drive is thereby transmitted to the two anchors, and therefore to the relative movement between the two bones. The distraction therefore takes place in a precisely defined direction. The advantageous consequence of this is that the form of the callous formed corresponds, at every point in time of the application, to the planned form. The new bone region growing out of the callous therefore has, after conclusion of the treatment, precisely the planned form and size.

The purely translational displacement of the anchors, without simultaneous rotation of the elements of the linear drive connected thereto, brings another further advantage. In the case of distraction osteogenesis, often the complete distraction device is implanted, with the exception of the adjustment head of the device, which in the case of the present device is located on the second end of the two aforementioned elements. In the case of devices according to the prior art, this means that the lead screw for displacing the anchors is also implanted, and for adjusting the anchors must be rotated relative to the surrounding tissue. In the device according to the invention, by contrast, for displacing the anchors, it is only necessary to displace an element with a smooth surface relative to the surrounding tissue.

DETAILED DESCRIPTION OF THE PREFERRED EMBODIMENTS

The effect achieved by means of an exact guidance of the linear drive is further supported in the present device by means of a suitable design of the anchors. According to a feature of the invention, it is provided for the anchors to have plate-shaped regions, which in a preferred embodiment are oriented perpendicularly to the displacement direction. This embodiment advantageously ensures a precise bracing of one anchor on the fixed bone and an exact support of the bone segment to be displaced by the other anchor. The displacement of the movable bone segment takes place in the last-mentioned embodiment of the distractor perpendicularly to the plate-shaped regions of the anchors and is therefore precisely predetermined.

A further advantage of the last-mentioned embodiment can be seen in the fact that one and the same design can be used for the left and right jaw halves and for applications in the upper jaw as well as the lower jaw. In the case of distractors according to the prior art, on the other hand, a "right" and a "left" distractor are usually required for the aforementioned applications.

In the design of the plate-shaped regions of the anchors, the invention proposes a plurality of advantageous solutions.

A first solution comprises anchors in which the plate-shaped regions are arranged eccentrically to the linear drive. This embodiment leads to the linear drive coming to lie in the edge region of the anchor. It permits an advantageous application of the distractor in which the plate-shaped region of at least one of the two anchors is introduced into a slit leading from the outside into the relevant bone segment, while the linear drive remains outside the bone.

The advantage of this embodiment can be seen in the fact that the distractor can be applied and removed with relatively little effort from the outside. This type of incorporation furthermore leads to the plate-shaped region of the relevant anchor being very stably seated in the bone. The distraction direction in the aforementioned application lies perpendicular to the orientation of the slit and—since the orientation of the slit can be very precisely defined—can be advantageously very precisely predetermined.

In an advantageous development of the aforementioned embodiment, it is provided that the thickness of the plate-shaped region of at least one anchor region tapers in a wedge-like way at the edges facing away from the linear drive. During insertion of the relevant anchor into the bone slit, the wedge-shaped edges are then pressed into the bone substance. By this means, the seating of the anchor in the bone issue is given even higher stability than in the aforementioned embodiment.

The same objective, of providing the distractor with a stable seat after its incorporation into the bone tissue, is also served by a further embodiment of the invention. Herein, it is provided also to design the outer surface of the linear drive as a wedge shape in the direction facing the eccentrically arranged plate-shaped regions. The wedge shape of the aforementioned outer surface is then pressed against the surface of the affected bone segment during incorporation of the distractor, and thereby also improves the seat of the distractor.

A decisive prerequisite for the usability of distractors in the jaw region are small dimensions of the distractor elements. Various measures in the development of distractors are therefore aimed at their miniaturisation. A further solution for designing the anchors follows precisely this goal. It is characterised in that the plate-shaped region of one anchor finds space within a recess of the plate-shaped region of the other anchor. In a completely retracted state of the distractor, both anchors therefore lie not one on top of the other, but one inside the other, and therefore cause only an overall height of the single thickness of the plate-shaped region. Distractors of this design can therefore be used within an osteomy section of low height.

For the design of the linear drive, the present invention proposes a solution in which the two displaceable elements run telescopically one inside the other. The invention provides two variants for this, a first in which both elements have a non-circular, preferably square cross-section, and a second in which both elements have a circular cross-section. In the latter variant, one of the elements is equipped with a longitudinal groove, in which a pin, which is rigidly connected to the other element, engages. In this case it is immaterial on which element the groove is provided and on which element the pin is fixed. The advantage of the proposed embodiment lies in the fact that it provides exact guidance while on the other hand permitting small dimensions of the drive with a view to miniaturisation.

The adjustment of the linear drive is carried out from the second end of the two elements. For the embodiment of the adjustment head, the invention provides for two variants:

In one variant, the outer of the two elements is equipped with an internal thread in the region of its second end, in which a nut with an external thread engages. The nut in turn has a concentrically arranged blind hole, which grips over the second end of the inner element with low play. In the case of a right-hand thread, a clockwise rotation of the nut leads to the nut disappearing continuously in the internal thread. Since, however, it is supported on the second end, which engages in the blind hole, of the inner element, in this process the outer element is displaced continuously towards its second end. The anchors fixed in each case on the two first ends of the elements in the process move away from one another, and the distance of the freely moving bone segment with respect to the fixed bones is continuously increased.

In the other variant, the roles of the inner and outer element are exchanged. Correspondingly, the inner of the two elements has, in the region of its second end, an external thread, in which a nut with an internal thread engages. The nut is in turn fixed so as to be rotatable on the outer element. In the case of a right-hand thread, a rotation of the nuts in the anticlockwise direction leads to the nut, and therefore to the outer element fixed on it, being displaced continuously towards its second end. The associated relative movements of the anchors fixed on the elements correspond to those of the above-mentioned variant.

For rotation of the nut in the case of the present distraction device, corresponding means are provided on that face end of the nut that faces away from the aforementioned elements. They comprise, for example, a hexagon for a nut key and/or a slit for a screwdriver.

The fastening of the anchors at the first end of the aforementioned element of the linear drive permits a plurality of constructional possibilities. It is of advantage for the use the device according to the invention for osteogenesis to fix the anchors in each case by means of a screw thread on the first end of the respective element. The thread ensures, on one hand, a reliable and rigid connection, however allows the possibility of separating the anchors and the aforementioned elements of the linear drive from one another. The latter option is of interest if the components of the distraction device are to be removed after conclusion of the treatment. In this case, the screw connection between the anchors and linear elements is detached in order subsequently to remove the components of the device from the treatment area.

In the design of the anchor fixture to the element of the linear drive as a detachable connection, it is expedient if the direction of rotation of the existing screw threads are in each case appropriately matched to one another. Correspondingly, in the variant of the device having an adjusting nut with external thread, it is proposed to design the thread of the aforementioned nut and the aforementioned anchors in each case with the same direction, preferably in each case as right-hand threads. In the variant of the device which has an adjusting nut with internal thread, on the other hand, it is expedient if the thread of the aforementioned nut and the aforementioned anchor are in each case of opposite direction. A solution is preferred here in which the thread of the nut is a right-hand thread and the threads of the aforementioned anchors are in each case designed as a left-hand thread.

These embodiments ensure that, with a rotation of the nut in the direction leading to an increase of the distance between the two anchors, the torque transmitted to the element by the nut favours a screwing of the aforementioned element into the anchors. Automatic release of the connection between the anchors and elements of the linear drive during an enlargement of the distraction zone is therefore eliminated. If on the other hand, it is required to remove the elements of the linear drive after conclusion of the treatment, a left-hand rotation is sufficient to release the connection between the aforementioned elements and the anchors.

Corresponding to the use of the distraction device for implantation in the human body, the material of the device is stainless steel. In particular, according to a feature of the invention, it is provided to produce the components of gold or platinum.

The invention provides for use of the proposed device in which, after conclusion of the distraction, it is removed again, as well as an application in which the device or components thereof remain in the patient's body. The latter case is of interest if the osteogenesis involves a subsequent reconstruction of the dentition. In this case it is proposed to use the components of the distraction device as dental implant posts, and to build up dental prostheses thereon. The advantage of this solution is obvious; it further obviates the intervention in the jaw required to produce the dentition after conclusion of the distraction treatment.

In the case of distraction devices that remain in the patient's body after conclusion of the distraction, the invention proposes embodiments in which the anchors are embodied centrically with respect to the linear drive. Anchors with plate-like geometries are preferred here, recesses being provided within the plate, which possess a twofold, threefold or manifold symmetry with respect to the axis of the linear drive. In the case of minimal bone supply, anchors are preferably used that have a star-shaped geometry and also have twofold, threefold or manifold symmetry.

In the case of distraction devices that are removed again after completed distraction, on the other hand, it is advantageous if—as already mentioned above—the anchors are arranged eccentrically to the linear drive and are formed as plate-shaped elements. The plate-shaped region of the anchors is hereby preferably designed in the form of a U.

Independently of the centric or eccentric arrangement, the invention provides for different types of fixing of the anchors. In a first variant, the plate-shaped regions of both anchors are arranged in the separating joint between movable and fixed bone segment. A further application is characterised in that the plate-shaped region of at least one of the two anchors is incorporated into the respective bone segment. A particularly stable seat of the distraction device can be hereby achieved in particular if both anchors are incorporated within the bone tissue.

BRIEF DESCRIPTION OF THE DRAWING FIGURES

Figure 1B:
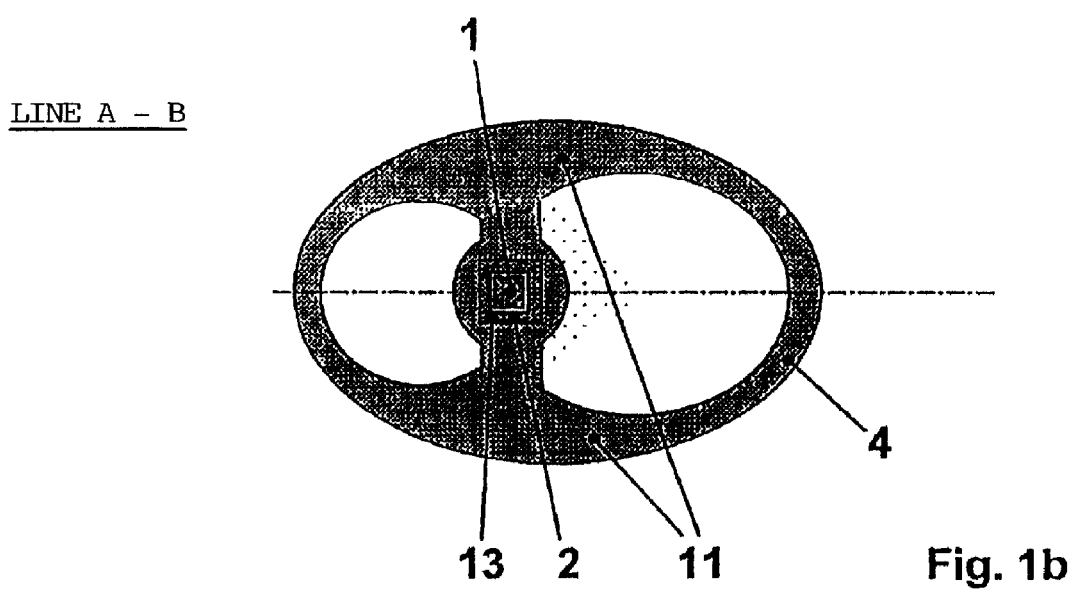

Further details, features and advantages of the invention can be derived from the subsequent part of the description. In this part, an exemplary embodiment of the device according to the invention for distraction osteogenesis is explained with reference to a drawing. The same reference characters in the individual figures here refer in each case to the same elements. In detail, FIG. 1a: shows a longitudinal section through the device FIG. 1b: shows a section corresponding to section plane AB in FIG. 1a FIG. 2: shows a longitudinal section through a variant of the device

DETAILED DESCRIPTION OF THE DRAWING FIGURES

FIG. 1 indicates the schematic construction of the distractor. The essential components comprise a linear drive with the elements 1 and 2 and the anchors 3 and 4 fixed on the respective ends 1a, 2a thereof. In the present embodiment, the elements 1, 2 run telescopically one inside the other, element 1 forming the inner element and element 2 the outer one. Both elements have non-circular cross-sections; element 1 has a square section and element 2 that of a four-square tube. The chosen embodiment of the linear drive ensures that the two elements 1, 2 of the drive are displaceable purely translationally with respect to one another, without rotation.

The adjustment of the linear drive is carried out by means of the adjustment head 5 of the second end 1b, 2b of the two elements 1, 2. The adjustment head 5 comprises a nut 6, which is equipped with an internal thread and is screwed on the inner element 2. The element 2 therefore has in the region 8 of its second end 2b, a corresponding external thread 7. The nut 6 is for its part fixed so as to be rotatable on the second end 2b of the outer element 2. The fixing of the aforementioned kind is indicated in the present diagram by means of the two clamps 9, 9'. In the right-hand thread 7 that forms the basis, a rotation of the nut 6 in the anticlockwise direction leads to the nut 6, and therefore the outer element fixed in it, being displaced continually towards the end 1b of the first element 1. The anchors fixed in each case on the two first ends 1a, 2a of the elements 1, 2 being hereby moved away from one another, and thus the distance 10 between them is increased.

In the application of the device for distraction osteogenesis, one anchor 4 is joined to the displaceable bone segment (not shown), and the other 3 to the fixed bone (not shown). The precise guidance of the linear drive hereby results in an equally precise movement of the displaceable bone segment. In the performance of the distraction, an increase of the distance 10 between the two anchors 3, 4 then leads to the callous occurring between the sides of the displaced and fixed bone becoming permanently enlarged, new bone tissue being thereby obtained.

As can be seen from FIG. 1, the anchors 3, 4 have plate-shaped regions 11, which ensure an exact support of one anchor 3 on the fixed bone and an exact support of the bone segment to be displaced by the other anchor 4.

In the present embodiment, the anchors 3, 4 are in each case fixed by means of a screw thread 12, 13 on the first end 1a, 2a of the respective element 1, 2. This type of fixing permits the anchors 3, 4 and the elements 1, 2 of the linear drive to be separated from one another and can be recommended if the components of the distraction device are to be removed again after conclusion of the treatment.

Where a right-hand thread 7 is specified for the nut 6, a left-hand thread 12, 13 in each case is to be provided for the anchor fixing. This embodiment ensures that, in the case of a rotation of the nut 6 in the anticlockwise direction for increasing the distance 10 between the two anchors 3, 4, the torques transmitted to the elements 1, 2 from the nut do not cause a release of the connection between the anchors 3, 4 and elements 1, 2 of the linear drive.

Figure 2:
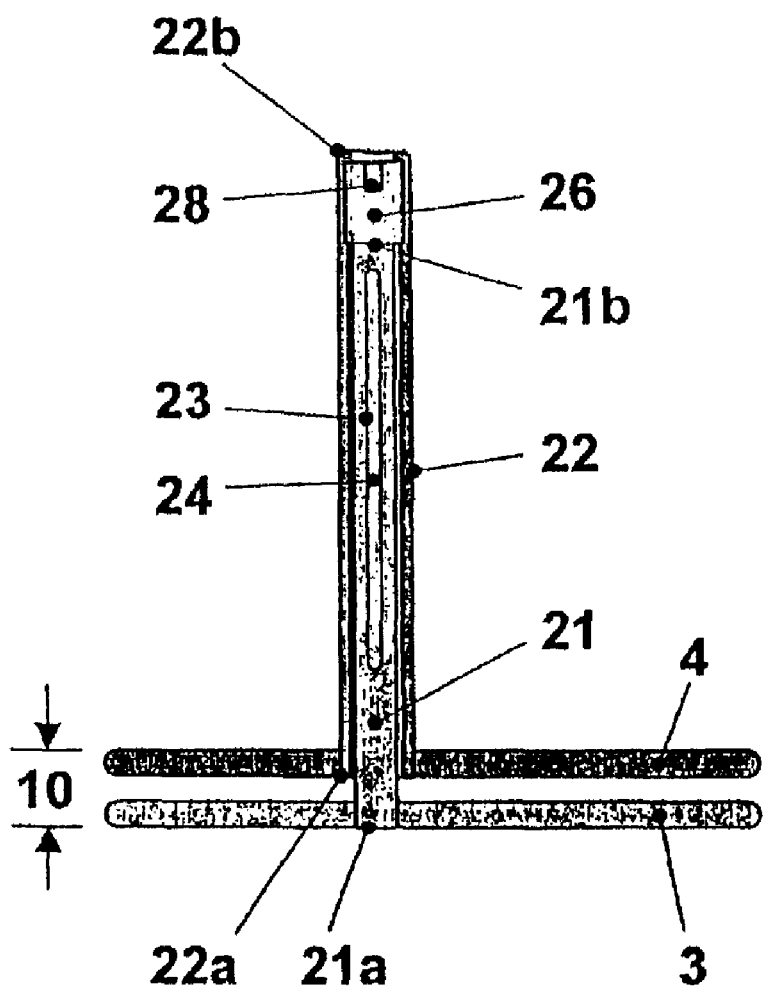

FIG. 2 shows a variant of the device in which the linear drive has a sleeve 22 with a circular internal cross-section and a pin 21, with a circular outer cross-section, running telescopically therein. A longitudinal groove 23 in the pin 21, in which a peg 24, which is rigidly connected to the sleeve 22, engages, ensures that the two elements 21, 22 do not rotate with respect to one another during movement of the linear drive. The movement of the linear drive is effected via a nut 26, which is seated on the second end 21b of the pin 21, and intermeshes with an internal thread of the sleeve 22. (Reference numeral "21a" denotes the first end of pin 21.) The external thread of the nut 26 and the internal thread of the sleeve 22 are not shown in the present drawing for the sake of clarity. The nut 26 is operated through a bore, which is produced in the face side on the second end 22b of the sleeve 22, by way of a screw driver (not shown), which intervenes in a slot in nut 26. The diameter of the bore is dimensioned such that a collar 28, which grips over the nut 26, remains on the sleeve.

With a right-hand thread on the nut 26 and sleeve 22, a rotation of the nut 26 (seen in the direction of the nut slit) in the clockwise direction leads to the nut 26 lifting the sleeve 22 and thereby the anchor 4, which is fixed on its first end 22a, and thus enlarging the distance 10 between the two anchors 3 and 4.

The invention claimed is:

1. An apparatus for vertical callus distraction, comprising: only a single linear drive comprising a first anchor with a plate-shaped region and a second anchor with a plate-shaped region with a recess being provided in said plate-shaped region of each of said first anchor and said second anchor, said first anchor and said second anchor being displaceable relative to one another via said linear drive and said plate-shaped region of said first anchor and said plate-shaped region of said second anchor being substantially orientated perpendicularly to a displacement direction, said first anchor being connectable to a fixed bone segment and said second anchor being connectable to a movable bone segment in a separating joint between said fixed bone segment and said movable bone segment, said linear drive further including a first element with said first anchor fixed to an end of said first element and a second element with said second anchor fixed to an end of said second element, said first element and said second element being translationally displaceable relative to one another and capable of establishing a rigidly defined distance between said first anchor and said second anchor with said linear drive preventing rotation of said first element relative to said second element, thereby preventing rotation between said first anchor relative to said second anchor.

2. The apparatus for vertical callus distraction according to claim 1, wherein said plate-shaped region of said first anchor and said plate-shaped region of said second anchor are eccentrically arranged relative to said linear drive.

3. The apparatus for vertical callus distraction according to claim 2, wherein said plate-shaped region of said first anchor has a thickness that tapers in a wedge-shaped manner at edges facing away from said linear drive.

4. The apparatus for vertical callus distraction according to claim 2, wherein said plate-shaped region of said first anchor and said plate-shaped region of said second anchor each have a thickness that tapers in a wedge-shaped manner at edges facing away from said linear drive.

5. The apparatus for vertical callus distraction according to claim 2, wherein said first element is telescopically insertable inside said second element.

6. The apparatus for vertical callus distraction according to claim 5, wherein said first element and said second element having a non-circular cross-section.

7. The apparatus for vertical callus distraction according to claim 6, wherein said non-circular cross-section of said first element and said second element is a square cross-section.

8. The apparatus for vertical callus distraction according to claim 5, wherein said first element and said second element each have a circular cross-section with said first element having a longitudinal groove into which a peg, rigidly connected to said second element, is engagable.

9. The apparatus for vertical callus distraction according to claim 2, wherein said first anchor and said second anchor are each fixed, via a screw thread, at said one end of said first element and said second element, respectively.

10. The apparatus for vertical callus distraction according to claim 1, wherein said end of first element is a first end, said first element further including a second end, and said end of said second element is a first end, said second element further including a second end, with said second element having an internal thread region as part of said second end for which a nut having an external thread engages, said nut having a concentrically arranged blind hole covering said second end of said first element with low play, with translational displaceability being generated by rotation of said nut.

11. The apparatus for vertical callus distraction according to claim 10, further comprising means for rotating said nut provided on a face side of said nut facing away from said first element and said second element.

12. The apparatus for vertical callus distraction according to claim 1, wherein said one end of first element is a first end, said first element further including a second end, said second end of said first element having an external thread wherein a nut having an internal thread engages, said nut being fixed to be rotatable on said second element, with translational displaceability being generated by rotation of said nut.

13. The apparatus for vertical callus distraction according to claim 12, further comprising means for rotating said nut provided on a face side of said nut facing away from said first element and said second element.

14. The apparatus for vertical callus distraction according to claim 1, wherein components of said linear drive are made of a noble metal.

15. The apparatus for vertical callus distraction according to claim 14, wherein said noble metal is gold.

16. The apparatus for vertical callus distraction according to claim 14, wherein said noble metal is platinum.

17. The apparatus for vertical callus distraction according to claim 1, wherein said first anchor and said second anchor have a two-fold symmetry.

18. The apparatus for vertical callus distraction according to claim 1, wherein said first anchor and said second anchor have a three-fold symmetry.

19. The apparatus for vertical callus distraction according to claim 1, wherein said first anchor and said second anchor have a manifold symmetry.

* * * * *